United States Patent [19]

Neuzil et al.

[11] Patent Number: 4,497,972
[45] Date of Patent: Feb. 5, 1985

[54] PROCESS FOR THE SEPARATION OF ETHYLBENZENE

[75] Inventors: Richard W. Neuzil, Downers Grove; Simon H. Hobbs, Oak Park, both of Ill.

[73] Assignee: UOP Inc., Des Plaines, Ill.

[21] Appl. No.: 540,931

[22] Filed: Oct. 11, 1983

[51] Int. Cl.$^3$ .......................... C07C 7/13; C10G 25/03
[52] U.S. Cl. ................................. 585/828; 208/310 Z
[58] Field of Search ..................... 208/310 Z; 585/828

[56] References Cited

U.S. PATENT DOCUMENTS

| | | | |
|---|---|---|---|
| 2,985,589 | 5/1961 | Broughton et al. | 585/826 X |
| 3,201,491 | 8/1965 | Stine et al. | 208/310 Z X |
| 3,265,750 | 8/1966 | Peck et al. | 585/825 |
| 3,510,423 | 5/1970 | Neuzil et al. | 585/825 |
| 3,558,730 | 1/1971 | Neuzil | 585/828 |
| 3,686,342 | 8/1972 | Neuzil | 585/825 |
| 3,732,325 | 5/1973 | Pharis et al. | 585/828 |
| 3,734,974 | 5/1973 | Neuzil | 585/828 |
| 3,917,734 | 11/1975 | deRosset | 585/828 |
| 3,943,182 | 3/1976 | Neuzil et al. | 585/828 |
| 3,997,620 | 12/1976 | Neuzil | 208/310 Z X |
| 4,021,499 | 5/1977 | Bieser | 585/828 |
| 4,028,428 | 6/1977 | Neuzil et al. | 585/828 |
| 4,029,717 | 6/1977 | Healy et al. | 208/310 Z X |
| 4,031,155 | 6/1977 | Healy et al. | 208/310 Z X |
| 4,108,915 | 8/1978 | Rosback et al. | 585/828 |
| 4,255,607 | 3/1981 | Miyake et al. | 585/825 X |
| 4,326,092 | 4/1982 | Neuzil | 585/828 |

Primary Examiner—Delbert E. Gantz
Assistant Examiner—Glenn A. Caldarola
Attorney, Agent, or Firm—James R. Hoatson, Jr.; Louis A. Morris; William H. Page, II

[57] ABSTRACT

A process for separating ethylbenzene from a feed mixture comprising ethylbenzene and at least one xylene isomer. The mixture is contacted with an adsorbent comprising a barium cation exchanged type-X zeolite containing from about 3.0 to about 6.0 wt. % H$_2$O. The unadsorbed portion of the feed mixture is removed from the adsorbent and the ethylbenzene recovered by desorption with benzene.

6 Claims, No Drawings

PROCESS FOR THE SEPARATION OF ETHYLBENZENE

BACKGROUND OF THE INVENTION

1. Field of the Invention

The field of art to which the claimed invention pertains is solid-bed adsorptive separation. More specifically, the claimed invention relates to a process for the separation of ethylbenzene from a feed mixture comprising ethylbenzene and at least one xylene isomer which process employs a solid adsorbent and desorbent combination which effects selective removal of ethylbenzene from the feed mixture.

2. Background Information

It is well known in the separation art that certain crystalline aluminosilicates can be used to separate hydrocarbons species from mixtures thereof. In particular, the separation of normal paraffins from branched chained paraffins can be accomplished by using the type A zeolite which have pore openings from 3 to about 5 Angstroms. Such a separation process is disclosed for example in U.S. Pat. Nos. 2,985,589 and 3,201,491. These adsorbents allow a separation based on the physical size differences in the molecules by allowing the smaller or normal hydrocarbons to be passed into the cavities within the crystalline aluminosilicate adsorbent, while excluding the larger or branched chain molecules.

U.S. Pat. Nos. 3,265,750 and 3,510,423 for example disclose processes in which larger pore diameter zeolites such as the type X or type Y structured zeolites can be used to separate olefinic hydrocarbons.

In addition to separating hydrocarbon types, the type X or type Y zeolites have also been employed in processes to separate para-xylene from a feed mixture comprising para-xylene and at least one other xylene isomer by selectively adsorbing para-xylene over the other xylene isomers. Such processes are disclosed in U.S. Pat. Nos. 3,732,325; 3,997,620; 4,029,717; 4,031,155; and 4,255,607. These references disclose various adsorbent (including Ba and K exchanged X-type zeolites) and desorbent combinations which effect selectivity for xylenes over ethylbenzene, but none teach benzene as a desorbent material, optimum water content of the adsorbent, nor, of course, ethylbenzene as the extract component.

Ethylbenzene is used as a raw material in the production of styrene monomer. Ethylbenzene can be and is commercially produced from the alkylation of benzene with ethylene. The cost of and competing demands for necessary benzene and ethylene feed streams have, however, prompted new efforts to recover ethylbenzene from various $C_8$ aromatic feed streams which already contain ethylbenzene. Such feed streams for instance, include $C_8$ aromatic extracts produced by a typical solvent extraction process from a pyrolysis gasoline or from a naphtha which has been reformed with a platinum-halogen-containing catalyst. Additionally $C_8$ aromatic cuts of hydrogenated pyrolysis naphthas or reformates prepared by fractionation without solvent extraction contain varying amounts of ethylbenzene.

Ethylbenzene can, of course, be separated from the xylene isomers by fractionation but because its boiling point is within about 4° F. of that of para-xylene, the fractionation can be achieved only with the more intricate super-fractionators. Typical ethylbenzene fractionators contain 300 to 400 actual trays and require about a 25–50 to 1 reflux to feed ratio. The process of our invention therefore offers a competitive alternative to the separation of ethylbenzene by super-fractionation.

U.S. Pat. No. 3,943,182 discloses a process for extracting ethylbenzene from admixture with xylenes which employs a type X zeolite having only Group I-A ions at exchangeable cationic sites, and which contains about 0.02 to 2.5 wt. % water. Benzene is mentioned as a possible but not preferred desorbent.

The present invention is based on the surprising discovery that, in contradistinction to much of the teaching in the art, an X type zeolite adsorbent having Ba exchanged cations is selective for ethylbenzene when the adsorbent contains an amount of water within a specified range and when benzene is employed as the desorbent. Furthermore, the adsorbent having such composition is superior to the adsorbent of U.S. Pat. No. 3,943,182 for the separation of ethylbenzene from admixture with xylenes.

SUMMARY OF THE INVENTION

It is, accordingly, a broad objective of our invention to provide a process for the separation of ethylbenzene from a feed mixture comprising ethylbenzene and at least one xylene isomer.

In brief summary, our invention is, in one embodiment, a process for separating ethylbenzene from a feed mixture comprising ethylbenzene and at least one xylene isomer which process comprises contacting said mixture with an adsorbent comprising a type X structured zeolite containing barium cations at exchangeable cationic sites. The adsorbent also contains from about 3.0 to 6.0 wt. % $H_2O$ measured by loss on ignition at 350° C. The contacting is effected at ethylbenzene adsorption conditions. The unadsorbed portion of the feed mixture is removed from the adsorbent and the adsorbed ethylbenzene is recovered from the adsorbent by contacting the adsorbent with benzene at desorption conditions.

Other embodiments and objects of the present invention encompass details about feed mixtrues, adsorbents, desorbents, and operating conditions all of which are hereinafter disclosed in the following discussion of each of these facets of the present invention.

DESCRIPTION OF THE INVENTION

Feed mixtures which can be utilized in the process of this invention will comprise ethylbenzene and at least one xylene isomer. Specifically, the feed mixture may contain ethylbenzene and para-xylene or meta-xylene or ortho-xylene. Possible feed mixtures can as well contain, in addition to ethylbenzene, any two xylene isomers or all three xylene isomers. The more typical feed mixtures will either be a mixture containing ethylbenzene and all three of the xylene isomers or a mixture containing ethylbenzene along with para-xylene and meta-xylene. Ortho-xylene which has a boiling point of about 6° F. higher than that of the nearest other $C_8$ aromatic (metal-xylene) can be separated by conventional fractionation techniques and hence may be previously removed from a feed mixture prior to its being charged to the process of this invention. Ortho-xylene fractionator towers for example will contain about 100 to 150 actual trays and will operate with about a 5–8 to 1 reflux to feed ratio.

Mixtures containing substantial quantities of ethylbenzene and xylene isomers generally are produced by reforming and isomerization processes. In reforming processes, a naphtha feed is contacted with a platinum-halogen-containing catalyst at severities selected to produce an effluent containing $C_8$ aromatic compounds which can be subsequently separated using the method of this invention. Xylene isomerization processes generally isomerize a xylene mixture deficient in one or more isomers to give an effluent containing approximately equilibrium quantities of the $C_8$ aromatic isomers which effluent can then be separated using the method of this invention. Generally the $C_8$ aromatics in such effluent stream will be concentrated by solvent extraction processes or by fractionation prior to being introduced into the process of this invention.

The equilibrium compositions of the xylene isomers and ethylbenzene at various temperatures are shown in Table 1 below.

TABLE 1

| Equilibrium $C_8$ Aromatic Compositions* | | | |
|---|---|---|---|
| Temperature, °C. | 327 | 427 | 527 |
| Mole percent of isomers | | | |
| Ethylbenzene | 6 | 8 | 11 |
| Para-Xylene | 22 | 22 | 21 |
| Meta-Xylene | 50 | 48 | 45 |
| Ortho-Xylene | 22 | 22 | 23 |

*Based on API sources

Since the ethylbenzene boils at about the same temperature as the meta-xylene and para-xylene isomers, fractionation methods are impractical for separating the ethylbenzene from meta- and para-xylene.

Feed mixtures may also contain small quantities of nonaromatics such as straight or branched chain paraffins, cycloparaffins, or olefinic materials. However, since separation of ethylbenzene from a feed mixture by selective adsorption of the ethylbenzene present in the feed mixture on a zeolite adsorbent apparently takes place because of a rather delicate acidity/basicity difference between ethylbenzene and the adsorbent compared to the xylene isomers and the adsorbent, it is preferred that these contaminants, especially olefins, be less than about 20 vol. % of the feed mixture passed into the process and more preferably less than about 10 vol. %.

To separate ethylbenzene from a feed mixture containing ethylbenzene and at least one xylene isomer, the mixture is contacted with the adsorbent and ethylbenzene is more selectively adsorbed and retained by the adsorbent while the less selectively adsorbed xylene isomer is removed from the interstitial void spaces between the particles of adsorbent and the surface of the adsorbent. The adsorbent containing the more selectively adsorbed ethylbenzene is referred to as a "rich" adsorbent—rich in the more selectively adsorbed ethylbenzene.

The more selectively adsorbed feed component is commonly referred to as the extract component of the feed mixture, while the less selectively adsorbed component is referred to as the raffinate component. Fluid streams leaving the adsorbent comprising an extract component and comprising a raffinate component are referred to, respectively, as the extract stream and the raffinate stream. As previously mentioned, the feed mixture can obtain more than one xylene isomer and it will therefore be recognized that all of the xylene isomers present in the feed mixture will be less selectively adsorbed with respect to ethylbenzene. Thus the raffinate stream will contain as raffinate components all of the xylene isomers appearing in the feed mixture and the extract stream will contain ethylbenzene as the extract component.

Although it is possible by the process of this invention to produce high purity (98% or greater, expressed as a percent of $C_8$ aromatics present) ethylbenzene at high recoveries, it will be appreciated that an extract component is never completely adsorbed by the adsorbent, nor is a raffinate component completely non-adsorbed by the adsorbent. Therefore, small amounts of a raffinate component can appear in the extract stream and, likewise, small amounts of an extract component can appear in the raffinate stream. The extract and raffinate streams then are further distinguished from each other and from the feed mixture by the ratio of the $C_8$ aromatic isomers appearing in the particular stream. More specifically, the ratio of the more selectively adsorbed ethylbenzene to the less selectively adsorbed xylene isomer will be highest in the extract stream, next highest in the feed mixture and lowest in the raffinate stream. Likewise, the ratio of the less selectively adsorbed xylene isomer to the more selectively adsorbed ethylbenzene will be highest in the raffinate stream, next highest in the feed mixture and lowest in the extract stream.

The adsorbent can be contained in one or more chambers where through programmed flow into and out of the chamber separation of the isomers is effected. The adsorbent may be contacted with a desorbent material which is capable of displacing the adsorbed extract component from the adsorbent. Alternatively, the adsorbed extract component could be removed from the adsorbent by purging or by increasing the temperature of the adsorbent or by decreasing the pressure of the chamber or vessel containing the adsorbent or by a combination of these means.

The adsorbent may be employed in the form of a dense compact fixed bed which is alternately contacted with the feed mixture and a desorbent material (hereinafter described). In the simplest embodiment of the invention the adsorbent is employed in the form of a single static bed in which case the process is only semi-continuous. A set of two or more static beds may be employed in fixed-bed contacting with appropriate valving so that the feed mixture is passed through one or more adsorbent beds while the desorbent material is passed through one or more of the other beds in the set. The flow of feed mixture and desorbent material may be either up or down through the adsorbent. Any of the conventional apparatus employed in static bed fluid-solid contacting may be used.

Moving bed or simulated moving bed systems, however, have a much greater separation efficiency than fixed adsorbent bed systems and are therefore preferred. Specifically, one preferred processing flow scheme which can be utilized to effect the process of this invention are those known in the art as simulated moving-bed countercurrent systems. One such system includes the flow scheme described in U.S. Pat. No. 2,985,589 issued to D. B. Broughton, incorporated herein by reference. This patent generally describes the processing sequence involved in a particular simulated moving-bed countercurrent solid-fluid contacting process.

Another embodiment of a simulated moving bed flow system suitable for use in the process of the present invention is the co-current high efficiency simulated moving bed process disclosed in our assignee's U.S. Pat.

No. 4,402,832, incorporated by reference herein in its entirety.

Adsorption and desorption in the process of our invention could be conducted both in the vapor phase or liquid phase or one operation may be conducted in the vapor phase and the other in the liquid phase. Operating pressures and temperatures for adsorption and desorption might be the same or different.

Preferred operating conditions for both adsorption and desorption include a temperature within the range of from about 20° to about 200° C. and a pressure selected to maintain liquid phase throughout the bed of adsorbent.

The desorbent materials which can be used in the various processing schemes employing a given adsorbent will vary depending on the type of operation employed. The term "desorbent material" as used herein means any fluid substance capable of removing a selectively adsorbed isomer from the adsorbent. In the swingbed system in which the selectively adsorbed isomer is removed from the adsorbent by a purge stream, gaseous hydrocarbons such as methane, ethane, etc. or other types of gases such as nitrogen or hydrogen may be used at elevated temperatures or reduced temperatures or reduced pressure or both to effectively purge the adsorbed isomer from the adsorbent.

However, in processes which are generally operated at substantially constant pressures and temperatures to insure liquid phase, the desorbent material relied upon must be judiciously selected in order that it may displace the adsorbed isomer from the adsorbent with reasonable mass flow rates and also without unduly preventing the adsorbed isomer from displacing the desorbent in a following adsorption cycle.

Desorbent materials should additionally be substances which are easily separable from the feed mixture that is passed into the process. In desorbing the preferentially adsorbed component of the feed, both desorbent and the extract component are removed from adsorbent in admixture. Without a method of separation of these two materials, the purity of the extract component of the feed stock would not be very high since it would be diluted with desorbent. It is contemplated that any desorbent material used will have a substantially different average boiling point than that of the feed mixture. More specifically, "substantially different" shall mean that the difference between the average boiling points shall be at least 20° F. The boiling range of the desorbent material could be higher or lower than that of the feed mixture. The use of a desorbent material having a substantially different average boiling point than that of the feed allows separation of desorbent material from feed components in the extract and raffinate streams by simple fractionation or other methods thereby permitting reuse of desorbent material in the process.

In the preferred isothermal, isobaric, liquid-phase embodiment of the process of our invention, proper selection of a desorbent material is critical to the successful operation of the process. Adsorptive selectivity of the particular adsorbent employed in our process for ethylbenzene with respect to xylene isomers as well as reasonable mass flow rates appears only when certain apparently unique desorbent materials are employed.

We have discovered a surprising effectiveness of benzene for a desorbent material in uniquely satisfying all of the above criteria when used with a barium cation exchanged X-type zeolite adsorbent discussed in greater detail hereinbelow.

One can appreciate that certain characteristics of adsorbents are highly desirable, if not absolutely necessary, to the successful operation of a selective adsorption process. Among such characteristics are: adsorption capacity for some volume of an extract component per volume of adsorbent; the selective adsorption of an extract component with respect to a raffinate component and the desorbent; and sufficiently fast rates of adsorption and desorption of the extract component to and from the adsorbent.

Capacity of the adsorbent for adsorbing a specific volume of an extract component (ethylbenzene in the process of our invention) is of course, a necessity; without such capacity the adsorbent is useless for adsorptive separation. Furthermore, the higher the adsorbent's capacity for an extract component the better is the adsorbent. Increased capacity of a particular adsorbent makes it possible to reduce the amount of adsorbent needed to separate the extract component contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life.

The second necessary adsorbent characteristic is the ability of the adsorbent to separate components of the feed or, in other words, that the adsorbent possess adsorptive selectivity, (B), for one component as compared to another component. Selectivity can be expressed not only for one feed as compared to another but can also be expressed between any feed mixture component and the desorbent. The selectivity, (B), as used throughout this specification is defined as the ratio of the two components of the adsorbed phase over the ratio of the same two components in the unadsorbed phase at equilibrium conditions.

Selectivity is shown as equation 1 below:

$$\text{Selectivity} = (B) = \frac{[\text{vol. percent } C/\text{vol. percent } D]_D}{[\text{vol. percent } C/\text{vol. percent } D]_U} \quad \text{Equation 1}$$

where C and D are two components of the feed represented in volume percent and the subscripts A and U represent the adsorbed and unadsorbed phases respectively. The equilibrium conditions as defined here were determined when the feed passing over a bed of adsorbent did not change composition after contacting the bed adsorbent. In other words, there was no net transfer of material occurring between the unadsorbed and adsorbed phases.

As can be seen where the selectivity of two components approaches 1.0 there is no preferential adsorption of one component by the adsorbent. As the (B) becomes less than or greater than 1.0 there is a preferential selectivity by the adsorbent of one component. When comparing the selectivity of the adsorbent of one component C over component D, A (B) larger than 1.0 indicates preferential adsorption of component C within the adsorbent. A (B) less than 1.0 would indicate that component D is preferentially adsorbed leaving an unadsorbed phase richer in component C and an adsorbed phase richer in component D. The preferred selectivity for an extract component is about 2.0. Desorbents ideally would have a selectivity equal to about 1 or slightly less than 1.

The third important characteristic is the rate of exchange of the adsorbed isomer with the desorbent or, in other words, the relative rate of desorption of the adsorbed isomer. This characteristic relates directly to the amount of desorbent that must be employed in the process to recover the adsorbed isomer from the adsorbent.

In order to test various adsorbents to measure the characteristics of adsorptive capacity and selectivity, a dynamic testing apparatus may be employed. The apparatus consists of an adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to analyze "on stream" the effluent stream leaving the adsorbent chamber.

A pulse test, performed using this apparatus and the following general procedure, is used to determine selectivities and other data for various adsorbent systems. The adsorbent is filled to equilibrium with a particular desorbent by passing the desorbent material through the adsorbent chamber. At a convenient time, a pulse of feed containing known concentrations of a nonadsorbed parafinnic tracer (n-nonane for instance) and of the particular $C_8$ aromatic isomers all diluted in desorbent is injected for a duration of several minutes. Desorbent flow is resumed, and the tracer and the aromatic isomers are eluted as in a liquid-solid chromatographic operation. The effluent can be analyzed by onstream chromatographic equipment and traces of the envelopes of corresponding component peaks developed. Alternatively, effluent samples can be collected periodically and later analyzed separately by gas chromatography.

From information derived from the chromatographic traces, adsorbent performance can be rated in terms of capacity index for an extract component, selectivity for one $C_8$ aromatic isomer with respect to the other, and the rate of desorption of extract component by the desorbent. The capacity index may be characterized by the distance between the center of the peak envelope of the selectively adsorbed $C_8$ aromatic isomer and the peak envelope of the tracer component or some other known reference point. It is expressed in terms of the volume in cubic centimeters of desorbent pumped during this time interval. Selectivity, (B), for the non-adsorbed isomer with respect to the adsorbed isometer may be characterized by the ratio of the distance between the center of the non-adsorbed isomer peak envelope and the tracer peak envelope (or other reference point) to the corresponding distance for the other (adsorbed) isomer. The rate of exchange of an adsorbed isomer with the desorbent can generally be characterized by the width of the peak envelopes at half intensity. The narrower the peak width the faster the desorption rate. The desorption rate can also be characterized by the distance between the center of the tracer peak envelope and the disappearance of a selectively adsorbed isomer which has just been desorbed. This distance is again the volume of desorbent pumped during this time interval.

To translate this type of data into a practical separation process requires actual testing of the best system in a continuous simulated moving bed liquid-solid contacting device. The general operating principles of a countercurrent type of such a device have been previously described and are found in Broughton U.S. Pat. No. 2,985,589. A specific laboratory-size apparatus utilizing these principles is described in deRosset et al U.S. Pat. No. 3,706,812. The equipment comprises multiple adsorbent beds with a number of access lines attached to distributors within the beds and terminating at a rotary distributing valve. At a given valve position, feed and desorbent are being introduced through two of the lines and raffinate and extract are being withdrawn through two more. All remaining access lines are inactive and when the position of the distributing valve is advanced by one index all active positions will be advanced by one bed. This simulates a condition in which the adsorbent physically moves in a direction countercurrent to the liquid flow. Additional details on the above-mentioned adsorbent testing apparatus and adsorbent evaluation techniques may be found in the paper "Separation of $C_8$ Aromatics by Adsorption" by A. J. deRosset, R. W. Neuzil, D. J. Korous and D. H. Rosback presented at the American Chemical Society, Los Angeles, Calif., Mar. 28 through Apr. 2, 1971.

Adsorbents used in the process of this invention are generally referred to as the crystalline aluminosilicates or molecular sieves and can comprise both the natural and synthetic aluminosilicates. Particular crystalline aluminosilicates encompassed by the present invention include crystalline aluminosilicate cage structures in which the alumina and silica tetrahedra are intimately connected in an open three dimensional network. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions. Thus, the crystalline aluminosilicates are often referred to as molecular sieves when the separation which they effect is dependent essentially upon distinction between molecule sizes as, for instance, when normal paraffins are separated from isoparaffins by using a particular crystalline aluminosilicate. In the process of this invention, however, the term molecular sieves is not strictly suitable since the separation of specific $C_8$ aromatic isomers is dependent on differences in the electrochemical attraction of different isomer configurations rather than pure physical size differences of the isomer molecules.

In hydrated form, the crystalline aluminosilicates generally encompass those zeolites represented by the Formula 1 below:

FORMULA 1

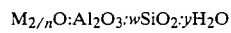

$$M_{2/n}O:Al_2O_3:wSiO_2:yH_2O$$

where M is a cation which balances the electrovalence of the tetrahedra and is generally referred to as an exchangeable cationic site, n represents the valence of the cation, w represents the moles of $SiO_2$ and y represents the moles of water. The cations may be any one of a number of cations which will be hereinafter described in detail.

The type X structured and type Y structured zeolites as discussed in this specification shall include crystalline aluminosilicates having a three dimensional interconnected cage structure and can specifically be defined by U.S. Pat. Nos. 2,882,244 and 3,130,007. The terms "type X structured" and "type Y structured" zeolites as used herein shall include all zeolites which have a general structure as represented in the above two cited patents and additionally shall specifically include those crystalline aluminosilicates produced from either of the zeolites described in U.S. Pat. Nos. 2,882,244 and 3,130,007 as starting materials by various exchange techniques or thermal treatments or combinations thereof to in any way modify the properties (such as pore diameter of cell size) of the type X or type Y zeolites starting material. In the most limiting sense only these terms refer to zeolite X and zeolite Y.

The type X structured zeolites can be represented in terms of mole oxides as represented in Formula 2 below:

FORMULA 2

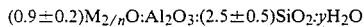
$(0.9 \pm 0.2)M_{2/n}O:Al_2O_3:(2.5 \pm 0.5)SiO_2:yH_2O$ where M represents at least one cation having a valence of not more than 3, n represents the valence of M and Y is a value up to about 9 depending upon the identity of M and the degree of hydration of the crystalline structure.

The type Y structured zeolite can be represented in terms of the mole oxides for the sodium form as represented by Formula 3 below:

FORMULA 3

$(0.9 + 0.2)Na_2O:Al_2O_3:wSiO_2:yH_2O$ where w is a value of greater than about 3 up to 8, and y may be any value up to about 9.

The term "exchangeable cationic sites" for the type X and type Y zeolites generally refers to the sites occupied by sodium cations present in the type X and type Y zeolites as indicated in Formula 2 and Formula 3 above and which can be replaced or exchanged with other cations to modify the properties of these zeolites.

Cationic or base exchange methods are generally known to those familiar with the field of crystalline aluminosilicate production. They are generally performed by contacting the sodium form of the zeolite with an aqueous solution of the soluble salt of the cation or cations desired to be placed upon the zeolite. After the desired degree of exchange takes place the sieves are removed from the aqueous solution, washed and dried to a desired water content. It is contemplated that cation exchange operations may take place by using individual solutions of the desired cations to be placed on the zeolite or by using an exchange solution containing a mixture of cations, where two or more desired cations are to be placed on the zeolite.

When singular cations are exchanged upon a zeolite the singular cations can comprise anywhere from 5 up to 75 wt. % on a relative volatile free basis of the zeolite depending upon the molecular weight of the material exchanged upon the zeolite. It is contemplated that when single ions are placed upon the zeolite that they may be on the zeolite in concentrations of from about 1% to about 100% of the original cations present (generally sodium) upon the zeolite prior to its being ion-exchanged. By knowing the empirical formula including the silica to alumina ratio of the zeolite used, its water content, and the percentage of binder used if any, it is possible to calculate the percentage of ion exchange that has taken place.

When two or more cations are placed upon the zeolite there are two parameters in which one can operate in order to effectively produce a zeolite having the maximum selective properties. One of the parameters is the extent of the zeolite ion exchange which is determined by the length of time, temperature and cation concentration. The other parameter is the ratio of individual cations placed on the zeolite. In instances in which two cations are exchanged upon the zeolite the weight ratio of these two respective components upon the zeolite can vary anywhere from about less than one up to about one hundred depending upon the molecular weight of the cations.

We have discovered the surprising and unexpected superiority of barium cation exchanged type X structured zeolite as an adsorbent for the process of the present invention when used in combination with benzene as a desorbent material. Preferably the zeolite will also contain potassium cations at exchangeable cation sites to achieve optimum rates of the transfer of benzene for the various components in the feed stream.

In the process of this invention we have additionally found a particular amount of water present on the zeolite adsorbent, as measured by loss on ignition at a certain temperature which is critical to the performance of the adsorbent. The amount of water present on the adsorbent is critical because too much water can decrease adsorptive capacities. On the other hand if the adsorbent is excessively dry ethylbenzene selectivity is decreased and the transfer rates are too slow. In this specification, the volatile matter (water) content of the zeolitic adsorbent is determined by first weighing the adsorbent and thereafter contacting the adsorbent in a high temperature furnace at a temperature of from about 350° C. to about 500° C. under an inert purge gas stream such as nitrogen for a period of time sufficient to achieve a constant weight. The sample is then cooled under an inert atmosphere and weighed to determine the difference in weight between the adsorbent before it was passed into the oven and afterwards. The difference in weight is calculated as a loss on ignition (LOI) and represents the volatile matter present on or within the adsorbent.

The exact mechanics by which water changes the adsorbent's selectivity for ethylbenzene with respect to the xylene isomers is not fully understood, but it is thought that in some way it increases the acidity of the adsorbent. Adsorbent water content is therefore an important process variable especially in continuous processing where the tendency might be for the adsorbent to pick up or lose water via the feed mixture and desorbent material with time. The water content of the adsorbent can be from about 3.0 to about 6.0 wt. % water as measured by loss on ignition at 350° C. without destroying ethylbenzene selectivity.

EXAMPLE 1

The following example is presented to illustrate, via the above discussed pulse test apparatus, the ability of the process of our invention to effect separation of ethylbenzene from all three xylene isomers. This example presents results of six pulse tests all using a barium cation exchanged X-type zeolite and benzene desorbent. In all but the first test the water content of the adsorbent was in the range of from about 3.0 to about 6.0 wt. %. Three of the six adsorbents tested also contained potassium cations, as preferred.

The testing apparatus was an adsorbent chamber containing approximately 70 cc of each adsorbent and was contained within a heat-control means in order to maintain essentially isothermal operations through the column. For each pulse test the column was maintained at a temperature of 150° C. and a pressure of 60 psig to maintain liquid-phase operations. Gas chromatographic analysis equipment was attached to the column effluent stream in order to determine the composition of the effluent material at given time intervals. The feed mixture employed for each test contained 5 vol. % ethylbenzene, 5 vol. % para-xylene, 5 vol. % meta-xylene, 5 vol. % ortho-xylene, 5 vol. % n-nonane which was used as a tracer and 75 vol. % desorbent material. The desorbent material employed was a mixture of 30 vol. % benzene and 70 vol. % normal heptane.

The operations taking place were as follows. The desorbent was run continuously at a nominal liquid hourly space velocity (LHSV) of 1.0 which amounted to about 1.17 cc per minute feed rate of desorbent. At some convenient time interval the desorbent is stopped and the feed is run for a ten-minute interval at 1 LHSV. The desorbent stream is then resumed at 1 LHSV and continued to pass into the adsorbent column until all the feed $C_8$ aromatics have been eluted from the column by observing the chromatograph generated by the effluent material leaving the adsorption column. The sequence of operations usually takes about an hour. The 10 minute pulse of feed and subsequent desorption may be repeated in sequence as often as is desired.

From information derived from the chromatographic traces selectivities of the adsorbents for ethylbenzene with respect to the xylene isomers (E/P, E/M and E/O) were calculated for each pulse test. Peak envelope widths and retention volumes were also measured. The results for the six pulse tests, 1 through 6, are shown in Table 1 below.

TABLE 1

| Exchanged Cation | 22 wt. % BaO + 6.5 wt. % $K_2O$ | | | | 30 wt. % BaO | |
|---|---|---|---|---|---|---|
| Wt. # $H_2O$ | Dry | 3.0 | 4.0 | 4.5 | 5.0 | 6.0 |
| Widths, cc | | | | | | |
| n-$C_9$ | 8.3 | 8.5 | 8.7 | 8.7 | 9.7 | 10.7 |
| EB | 15.6 | 17.6 | 14.5 | 11.4 | 13.6 | 17.7 |
| p-X | 16.6 | 13.3 | 13.1 | 14.4 | 19.5 | 18.9 |
| m-X | 15.4 | 12.7 | 13.7 | 14.2 | 18.1 | 20.4 |
| o-X | 17.0 | 12.4 | 12.9 | 13.3 | 17.2 | 21.1 |
| Ret. Vols., cc | | | | | | |
| EB | 27.7 | 31.4 | 24.3 | 18.7 | 24.2 | 18.1 |
| p-X | 30.7 | 20.0 | 14.4 | 9.4 | 13.7 | 7.9 |
| m-X | 21.0 | 12.6 | 10.6 | 9.0 | 12.4 | 10.1 |
| o-X | 29.6 | 20.1 | 15.6 | 11.5 | 16.7 | 10.8 |
| Bs | | | | | | |
| E/P | 0.9 | 1.57 | 1.69 | 1.99 | 1.77 | 2.29 |
| E/M | 1.32 | 2.49 | 2.29 | 2.08 | 1.95 | 1.79 |
| E/O | 0.94 | 1.56 | 1.56 | 1.63 | 1.45 | 1.68 |

It is first immediately apparent that the dry adsorbent does not even exhibit selectivity for ethylbenzene and is thus of no utility in the separation of the present invention. Furthermore, data for the use of barium cation exchanged X-type zeolite with desorbents other than benzene is not presented, since, as discussed above, it is known in the art that such adsorbent/desorbent combinations exhibit selectivity for one or more of the xylenes over ethylbenzene. The data, of course, does show a consistent selecivity for ethylbenzene of the adsorbent-/desorbent/water content combinations of the present invention.

It should be further noted that the peak widths for the xylene isomers are lower for the preferred potassium cation containing adsorbent which is indicative of a desirable more rapid rate of removal of these isomers from the adsorbent by the desorbent.

EXAMPLE 2

The feasibility of separating ethylbenzene from a feed mixture comprising ethylbenzene and at least one xylene isomer by selective adsorption of ethylbenzene, which was demonstrated by pulse test results, was confirmed by continuous testing in a laboratory-sized embodiment of the countercurrent simulated moving bed apparatus described above and referred to as a carousel unit.

The adsorption column of the carousel unit was packed with 462 ml. of barium and potassium exchanged X-type zeolite containing 4–5 wt. % water and divided into twenty-four beds. The feed composition comprised a $C_8$ aromatic and n-octane mixture further described in the following Table 2. The desorbent comprised pure benzene. Other operating parameters were as follows:

| A/F | 2.0 (based on selective pore volume = 12% of bed volume) |
|---|---|
| $\theta$, hrs | 0.75 |
| $L_1/A$ | 1.15 |
| $L_2/A$ | 0.37 |
| $L_3/A$ | 1.31 |
| $L_4/A$ | −1.76 |
| Temperature | 130° C. | where A is the selective pore volume circulating per hour, F is the feed rate; $\theta$ is the valve cycle time of the moving bed system; and $L_1$, $L_2$, $L_3$ and $L_4$ are the liquid flow rates into zones I, II, III and IV, respectively, less the void volume of each respective zone.

The results of the carousel test run are given in the following Table 2.

TABLE 2

Carousel Results of Ethylbenzene Separation
Averages from samples acquired over a two-hour period.

| | Feed Wt. % | Extract Wt. % | Raffinate Wt. % |
|---|---|---|---|
| Ethylbenzene | 24.1 | 99.3 | 1.4 |
| n-Octane | 4.1 | — | 5.4 |
| p-Xylene | 17.4 | 0.2 | 22.3 |
| m-Xylene | 39.6 | 0.4 | 51.1 |
| o-Xylene | 14.8 | 0.1 | 19.8 |

Ethylbenzene Extraction Efficiency = 95.5%

The effectiveness of the present invention in an actual simulated moving bed environment is clearly demonstrated by the data of Table 2.

We claim as our invention:

1. A process for separating ethylbenzene from a feed mixture containing ethylbenzene and at least one xylene isomer which comprises contacting said mixture with an adsorbent comprising X structured zeolite containing barium cations at exchangeable cationic sites and which contains from about 3.0 to 6.0 wt% $H_2O$ measured by loss on ignition at 350° C., said contacting being at ethylbenzene adsorption conditions to adsorb said ethylbenzene in the adsorbent, removing the unadsorbed portion of said feed mixture from said adsorbent containing at least one xylene isomer and recovering adsorbed ethylbenzene from said adsorbent by contacting said adsorbent with benzene desorbent at desorption conditions and withdrawing from said adsorbent a stream comprising ethylbenzene and benzene.

2. The process of claim 1 wherein said zeolite also contains potassium cations at exchangeable cationic sites.

3. The process of claim 1 wherein said adsorption and desorption conditions comprise a temperature from about 20° to about 200° C. and a pressure sufficient to maintain liquid phase.

4. The process of claim 1 wherein said process is effected by means of a simulated moving bed flow system.

5. The process of claim 4 wherein said simulated moving bed flow system is of the countercurrent type.

6. The process of claim 4 wherein said simulated moving bed flow system is of the co-current high efficiency type.

* * * * *